United States Patent
Chen et al.

(10) Patent No.: US 11,066,338 B2
(45) Date of Patent: *Jul. 20, 2021

(54) ANTIMICROBIAL GLAZE AND PORCELAIN ENAMEL VIA DOUBLE LAYER GLAZE WITH HIGH ZINC CONTENT

(71) Applicant: IDEAL STANDARD INTERNATIONAL NV, Zaventem (BE)

(72) Inventors: Zheng Chen, Flemington, NJ (US); James Michael McHale, Hillsborough, NJ (US)

(73) Assignee: AS America, Inc., Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/588,677

(22) Filed: Sep. 30, 2019

(65) Prior Publication Data

US 2020/0095173 A1 Mar. 26, 2020

Related U.S. Application Data

(63) Continuation of application No. 11/920,111, filed as application No. PCT/US2006/017366 on May 5, 2006, now Pat. No. 10,427,986.

(60) Provisional application No. 60/679,620, filed on May 9, 2005.

(51) Int. Cl.

| | | |
|---|---|---|
| C04B 41/52 | (2006.01) | |
| A01N 59/16 | (2006.01) | |
| C03C 8/02 | (2006.01) | |
| C03C 8/04 | (2006.01) | |
| C03C 8/14 | (2006.01) | |
| C04B 41/00 | (2006.01) | |
| C04B 41/89 | (2006.01) | |
| C04B 111/20 | (2006.01) | |

(52) U.S. Cl.
CPC ............ *C04B 41/52* (2013.01); *A01N 59/16* (2013.01); *C03C 8/02* (2013.01); *C03C 8/04* (2013.01); *C03C 8/14* (2013.01); *C04B 41/009* (2013.01); *C04B 41/89* (2013.01); *C03C 2204/02* (2013.01); *C04B 2111/2092* (2013.01)

(58) Field of Classification Search
CPC .................................................... C04B 41/52
See application file for complete search history.

*Primary Examiner* — Kyle A Purdy
(74) *Attorney, Agent, or Firm* — Tyler A. Stevenson; Anna-Lisa L. Gallo

(57) ABSTRACT

A cost-effective and practical antimicrobial glaze system and glazing process is disclosed herein. The antimicrobial glaze/enamel may comprise at least two layers: a base layer and a top layer. The base layer may contain a typical or normal glaze widely used in sanitary ware, having a low level of zinc oxide. The base layer glaze may be directly sprayed on the clay body surface. A thin top glaze layer is sprayed on top of the base glaze layer and the top layer may contain a high level of zinc oxide.

21 Claims, 2 Drawing Sheets

ANTIMICROBIAL GLAZE AND PORCELAIN ENAMEL VIA DOUBLE LAYER GLAZE WITH HIGH ZINC CONTENT

This application is a continuation of U.S. application Ser. No. 11/920,111, filed on Nov. 19, 2008, which is a national stage application, filed under 35 U.S.C. § 371, of International Patent Application No. PCT/US2006/017366, filed on May 5, 2006, which claims priority to U.S. Provisional Patent Application No. 60/679,620 filed May 9, 2005, all of which are incorporated herein by reference in their entirety.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to antimicrobial sanitary ware, in particular, the ceramic glaze layer. The invention provides for a cost-effective and practical antimicrobial glaze system and glazing process.

BACKGROUND OF THE INVENTION

The oligodynamic effect is the term given to the ability of small amounts of heavy metals to exert a lethal effect on bacteria (from the Greek: oligos, small; dynamis, power). The effectiveness of heavy metals as antimicrobials is believed to be due to the high affinity of cellular proteins for metallic ions. Bacteria cells die due to the cumulative effects of ions within the cell, even if the concentration of ions in a solution is miniscule. Metals that generally show a strong oligodynamic effect are (in order of decreasing strength) Hg>Ag>Cu>Zn>Fe>Pb>Bi. Among these metals, silver and zinc have been used in materials for various applications and industries, such as materials for use in medical devices, food processing products, textiles, and sanitary ware. Oligodynamic elements other than silver and zinc, either due to human toxicity or some incompatibility with the intended matrix material (e.g. changes in color), are rarely used as antimicrobial agents in material applications, Compared to zinc, silver and its salts exert a much stronger antimicrobial effect against common bacteria such as *Staphylococcus Aureus* and *Escherichia coli*. Zinc oxide, however, generally shows much better efficacy than silver against various fungi. Another practical factor from a manufacturing standpoint is that silver is far more expensive than zinc, with a market price over 100 times greater per unit weight compared to zinc.

U.S. Pat. Nos. 5,807,641 and 5,882,808 relate to antimicrobial sanitary ware produced by adding silver compounds to the ceramic glaze layer. The silver is added to the glaze slurry as a salt or oxide. The glaze slurry is applied to the ceramic body and fired at a temperature generally exceeding 1100° C. This approach can provide good antibacterial efficacy, but in practice, the level of silver required to obtain this effect results in an unacceptably large increase in the cost of the glaze. For example, a typical toilet and tank combination contains about 6.5 lbs of glaze. Due to the relatively high vapor pressure of silver and its compounds at temperatures above 1200° C., at least 2 wt % of an antimicrobial silver compound is needed to impart strong antimicrobial efficacy to the fired sanitaryware body. The cost of antimicrobial silver compounds is roughly $100/lb, which at 2% loading results in an added cost of $13 per toilet and tank combo. This cost requires a price increase for antimicrobial sanitaryware that is well beyond what many consumers in the Americas and Europe are willing to pay for the feature. Additionally, a large part of the silver in the glaze vaporizes and condenses on the walls of the kiln, which over time can build up to troublesome levels and result in manufacturing downtime, thereby further increasing the cost of manufacturing these pieces. Thus, there is a need for a more cost effective means than using silver for producing antimicrobial sanitaryware for these markets.

Of the other metals that have strong oligodynamic effects, zinc is most suited for use in sanitaryware applications. Mercury, lead, and bismuth present toxicity and/or environmental issues, whereas iron and copper compounds would eliminate the possibility of producing white pieces. Zinc oxide is already used as a flux material in some sanitaryware glaze systems, albeit at levels that are too low to yield any significant antimicrobial effect. For example, Japanese Patent Application 10-227686 relates to an antimicrobial glaze formulation that contains 6-20 wt % of zinc compounds measured as zinc oxide. The inventors state that at least 6 wt % of zinc compounds is necessary to obtain consistent antimicrobial efficacy. Using such a large amount of zinc in a sanitaryware glaze system, although it might provide antimicrobial properties at a cost much lower than that obtainable through the use of silver compounds, presents manufacturing issues that severely limit the practicality of this approach. Such a sanitary ware glaze system having more than 6 wt % zinc oxide, will begin to suffer severe pitting and surface irregularity defects. These defects become even more severe if the circulation of air in the kiln is not sufficient.

Similar needs and issues exist for antimicrobial porcelain enamel systems. Whereas glazes are glass coatings applied to ceramic substrates (bodies), porcelain enamel is the general term applied to such glass coatings on metallic substrates. For example, porcelain enamels are widely applied to steel and cast iron bodies in the manufacture of sinks, bathtubs, hot water heaters, cookware, and some appliances.

SUMMARY OF THE INVENTION

Therefore, there remains a need for a cost-effective and practical (from a manufacturing viewpoint) approach to providing sanitary ware with antimicrobial properties. The invention described herein provides a solution to this problem. A cost-effective and practical antimicrobial glaze/enamel system and glazing process can be achieved by the herein described glazing technology, employing at least two glaze layers.

The antimicrobial glaze/enamel of the present invention is made of at least two layers: a base layer and a top layer. The base layer consists of typical glaze materials that are widely used in sanitary ware manufacture. The base layer glaze is sprayed directly onto the clay body surface. The top layer contains a high level of zinc oxide (ZnO). The level of ZnO in the top layer is between about 8.0 wt % to about 35.0 wt %, preferably about 10.0 wt % to about 25.0 wt %. The top layer thickness may be in the range between about 25 μm to about 250 µm, and preferably about 25 µm to about 150 µm in order to achieve good glaze quality.

These and other embodiments are disclosed or are obvious from and encompassed by, the following Detailed Description.

BRIEF DESCRIPTION OF THE DRAWINGS

These and other objects and features are illustrated and described in the following specification to be read in conjunction with the sheets of drawings in which.

DETAILED DESCRIPTION OF THE INVENTION

Figure 1:
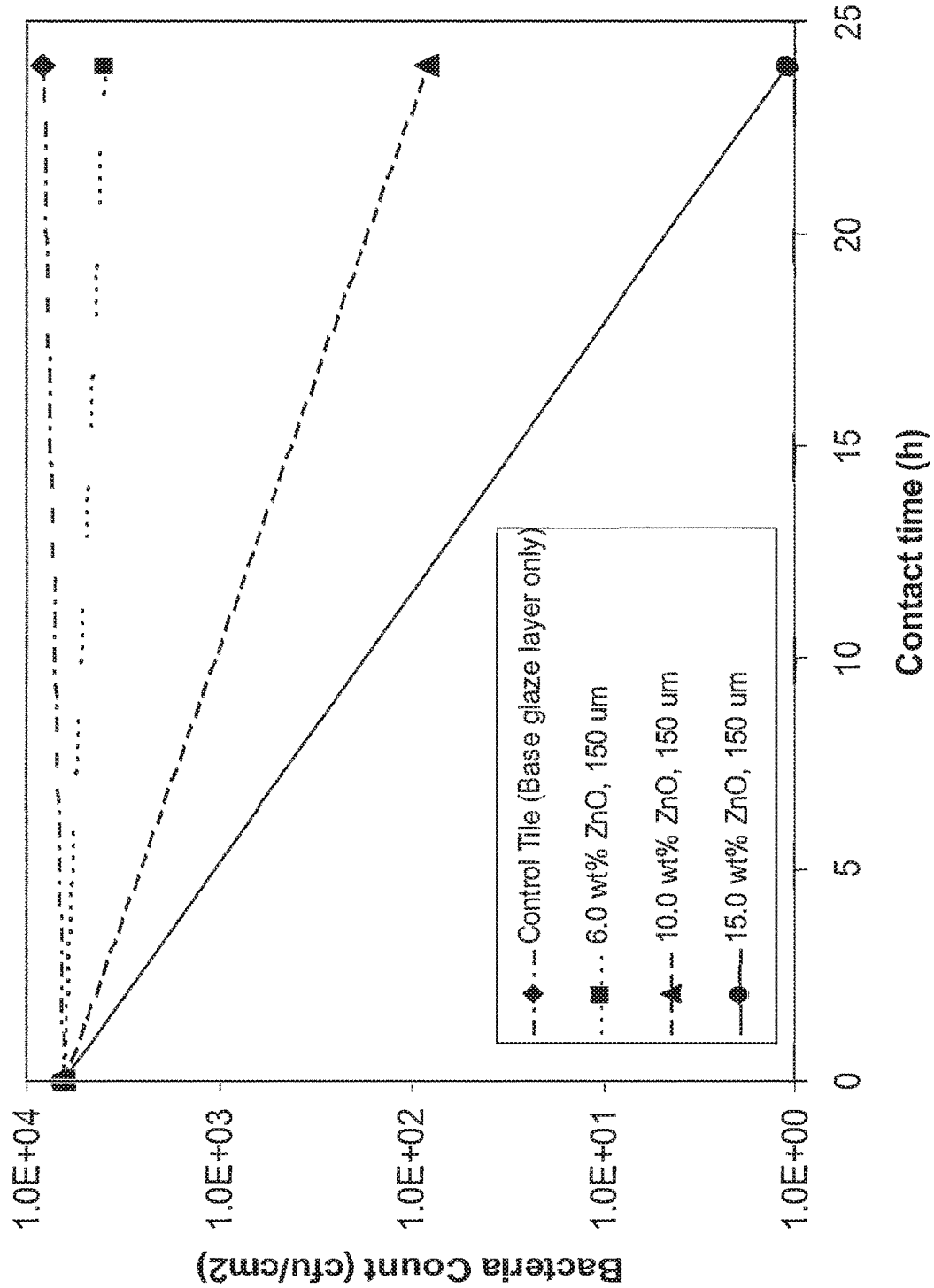
FIG. 1 is a chart comparing the antimicrobial efficacy of ceramic tile samples with thin top glaze layers containing 6.0, 10.0, and 15.0 weight percent zinc oxide relative to a ceramic control tile with no top layer. The top glaze layers of the samples compared in FIG. 1 are approximately 150 µm thick.

The antimicrobial glaze/enamel of the present invention is made of at least two layers: a base layer and a top layer. The base layer consists of typical glaze materials that are widely used in sanitary ware manufacture. The base layer glaze is sprayed directly onto the clay body surface. The top layer contains a high level of zinc oxide (ZnO). The level of ZnO in the top layer is between about 8.0 wt % to about 35.0 wt %, preferably about 10.0 wt % to about 25.0 wt %. The top layer thickness may be in the range between about 25 µm to about 250 µm, and preferably about 25 to about 150 µm in order to achieve good glaze quality.

A typical glaze formula, an example of which is listed in Table 1, is used as the first layer (base layer), and may be sprayed on the clay body surface directly. The thickness of the base glaze layer is preferably in the range of about 300 µm to about 600 µm. With about 0 wt % to about 8.0 wt % ZnO in the base layer, the glaze can be made free of pits and other surface irregularity defects. The base layer is then dried or fired. After firing a typical base glaze layer composition may be that shown in Table 2.

TABLE 1

Typical glaze formula used in base layer.

| Raw Materials | Formula (wt %) |
|---|---|
| Feldspar | 32.0-42.0 |
| Whiting | 8.0-18.0 |
| ZnO | 0-8.0 |
| Talc | 0-3.0 |
| Frit | 0-10.0 |
| Silica | 13.0-23.0 |
| Opacifier | 7.0-15.0 |
| Clay | 0-12.0 |
| Other | <10.0 |

TABLE 2

Typical composition of base glaze after firing.

| Chemical Ingredients | Formula (wt %) |
|---|---|
| SiO2 | 40-70 |
| Al2O3 | 0-15 |
| ZrO2 | 0-15 |
| ZnO | 0-8 |
| CaO | 0-20 |
| TiO2 | 0-20 |
| B2O3 | 0-20 |
| Others (e.g., K2O, Na2O, MgO, Li2O) | 0-20 |

After the base layer is dried or fired, preferably dried in air at a temperature below about 200° C., a second, top glaze layer with a higher ZnO level than the base layer is sprayed on the top of the base layer. To avoid the formation of surface defects, the thickness of the top glaze layer is maintained at 25 µm to 250 µm. To achieve sufficient antimicrobial efficacy, the ZnO level in the top glaze layer glaze is between about 8.0 wt % and about 35.0 wt %.

An example of a top glaze layer formula after firing is listed in Table 3. In order to reduce the possibility of the top glaze layer forming pits and other surface defects, that layer is kept thin and more exposed to air circulation. The surface of the top glaze layer is smooth, uniform, and has a high gloss. For optimal efficacy, surface appearance, and gloss, the top layer thickness needs to be in the range of about 25 µm to about 250 vim, preferably about 100 pin to about 200 µm. After finishing spraying of the top glaze layer, the parts can be sent to kiln for firing at normal firing temperature, typically around 1200° C.

TABLE 3

Top layer glaze composition (after firing)

| Raw Materials | Formula (wt %) |
|---|---|
| Al₂O₃ | 8 |
| SiO₂ | 61 |
| ZnO | 25 |
| Other Flux | 6 |

Because only a thin layer contains high levels of ZnO, the total ZnO content in the overall glaze is less than about 5.0 wt %. As the cost of ZnO is about $1/lb, a glaze system that requires about 5.0% ZnO can be manufactured at about 1/50$^{th}$ of the cost of a glaze with about 2.0 wt % of antimicrobial silver compound. The zinc-based glaze will give equal or better antimicrobial performance because the surface of the glaze in contact with bacteria can have a zinc content that is orders of magnitude higher than the silver content in commercially available antimicrobial chinaware.

To summarize the present invention, the antimicrobial glaze/enamel is made of at least two layers: a base layer and a top layer. The base glaze layer consists of typical or normal glaze which is widely used in sanitary ware, and preferably has low levels of ZnO; about 0-8.0 wt %. An example of a base glaze layer composition after firing is shown in Table 3. The base glaze layer is preferably between 300 µm and 1000 µm thick after firing.

The base glaze layer is sprayed directly on the clay body surface. The top glaze layer material contains high ZnO levels in the range of between about 6.0 wt % and about 35.0 wt %, preferably about 10.0 wt % to about 25.0 wt %. Other ingredients in the top layer may include, but are not limited to, Al₂O₃, SiO₂, and other oxides, such as, but not limited to, $K_2O$, $Na_2O$, $Li_2O$, MgO, CaO, $B_2O_3$, BaO, MoO, SnO, and SrO The top layer's thickness needs to be controlled in the range of between about 25 μm to about 250 μm, and preferably from about 25 μm to about 150 μm in order to achieve good glaze quality.

In another embodiment, a top glaze layer is sprayed and fired to a thickness of between about 25 μm and 250 μm in which the top 10 μl of the top glaze layer have between 8.0 wt % and 15.0 wt % ZnO, but due to diffusion between the top glaze layer and the bottom glaze layer the overall wt % ZnO in the top layer is less than 8.0 wt %.

In another embodiment, oligodynamic elements or compounds other than zinc are added to increase the antimicrobial efficacy of the glaze or enamel, including but not limited to Hg, Ag, Cu, Fe, Pb, Bi, and/or a rare earth element or elements.

The invention will now be further described by way of the following non-limiting examples.

EXAMPLES

Example 1

A series of ceramic tiles were prepared with base layer compositions according to Table 1 and top layer compositions containing 6.0 wt %, 10.0 wt %, 15.0 wt %, and 25.0 wt % ZnO. The base layer was sprayed to give a post-fire thickness of approximately 450 μm. After allowing approximately 5 minutes for the base layer to dry in ambient air, the top layer was sprayed on to the base layer to a post-fire thickness of approximately 150 μm. The tiles were then fired in air at a temperature of 1215° C. for a soak time of 45 minutes. Upon cooling and removal from the furnace, the samples were subjected to antimicrobial efficacy testing in accordance with the procedures outlined in the Japanese Standard JIS Z2801. A ceramic tile with the identical base layer and no top layer was prepared at the same time and used as the control tile. The results of these tests are shown in Table 4 and FIG. 1. The results indicate that the sample with 6 wt % ZnO in the top layer has little of no efficacy against *Staph Aureus* relative to the control tile with no top layer glaze. The sample with top layer glaze containing 10 wt % ZnO exhibited significantly improved antimicrobial efficacy compared to the 6.0 wt % ZnO glaze, with a roughly Log 2.0 reduction relative to the control tile. The sample with top layer glaze containing 15.0 wt % ZnO exhibited a Log 3.8 reduction relative to the control tile. This corresponds to a reduction in *Staph Aureus* count of 99.98% over the 24 hour test period. Additionally, the antimicrobial efficacy of the sample having 25.0 wt % ZnO in the top layer (not shown) exhibited a >Log 3.0 reduction against *Staph Aureus*. However, the cosmetic quality of the glaze began to suffer from surface defects due to the high ZnO content.

Example 2

Figure 2:
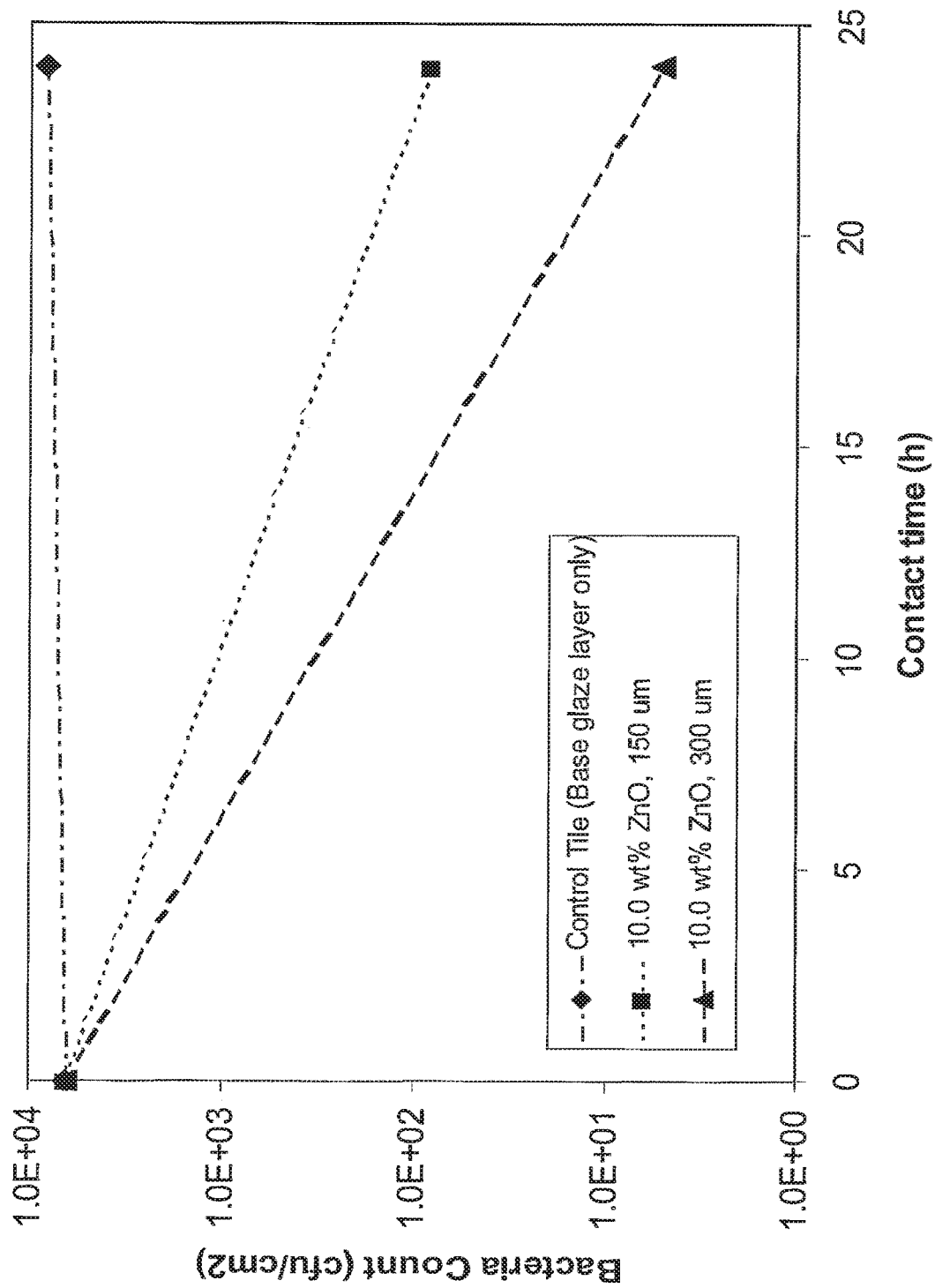
FIG. 2 is a chart comparing the antimicrobial efficacy test results of ceramic tile samples that have top layers containing 10.0 weight percent zinc oxide at a thickness of 150 µm and 300 µm. The efficacy is reported relative to ceramic control tiles with no top layer glaze.

Additional sample tiles were prepared according to the procedure given in Example 1, with the exception that the post-fire thickness of the top layer was varied from 150 μm to 300 μm. These samples were then subjected to antimicrobial efficacy testing in accordance with the procedures outlined in the Japanese Standard JIS Z2801. FIG. 2 shows the difference in antimicrobial efficacy against *Staph Aureus* of samples with a 10 wt % ZnO top glaze layer at different thickness. The efficacy is improved when the thickness is increased from 150 μm to 300 μm.

TABLE 4

Bacteria counts (in colony forming units/$cm^2$) during JIS Z2801 testing of samples described in Example 1.

| | Contact time against Staph Aureus | |
|---|---|---|
| ZnO level in top glaze layer | 0 hours | 24 hours |
| Control Tile (0% ZnO) | $6.5 \times 10^3$ | $8.3 \times 10^3$ |
| 6.0 wt % ZnO, 150 μm | $6.5 \times 10^3$ | $4.0 \times 10^3$ |
| 10.0 wt % ZnO, 150 μm | $6.5 \times 10^3$ | $8.3 \times 10^1$ |
| 15.0 wt % ZnO, 150 μm | $6.5 \times 10^3$ | $1.1 \times 10^0$ |

Having thus described in detail the preferred embodiments of the present invention, it is to be understood that the invention defined by the above paragraphs is not to be limited to the particular details set forth in the above description. Many apparent variations thereof are possible without departing from the spirit or scope of the present invention.

In this application, terms such as "comprises", "comprised", "comprising" and the like, can have the meaning attributed to it in U.S. patent law; e.g., they can mean "includes", "included", "including", and the like; and terms such as "consisting essentially of" and "consists essentially of," have the meaning ascribed to them in U.S. patent law, e.g., they allow for elements not explicitly recited, but exclude elements that are found in the prior art or that affect a basic or novel characteristic of the invention.

Citation or identification of any document in this application is not an admission that such document is available as prior art to the present invention.

What is claimed is:

1. Sanitary ware comprising a multilayer antimicrobial ceramic glaze, the ceramic glaze comprising
   a base glaze layer containing from 0.0 percent by weight to about 8.0 percent by weight ZnO; and
   a top glaze layer containing from about 8.0 percent by weight to about 35.0 weight percent ZnO,
   wherein a total ZnO content in the multilayer glaze is less than 5.0 weight percent.

2. The sanitary ware of claim 1, wherein the top layer contains from about 10.0 weight percent to about 25.0 weight percent ZnO.

3. The sanitary ware of claim 1, wherein the base layer contains ZnO.

4. The sanitary ware of claim 1, wherein the base layer contains from about 0.0 weight percent to about 6.0 weight percent ZnO.

5. The sanitary ware of claim 1, wherein the ceramic glaze is substantially free of surface defects.

6. The sanitary ware of claim 1, wherein the base glaze layer is from about 300 μm to about 1000 μm thick.

7. The sanitary ware of claim 1, wherein the base glaze layer is from about 300 μm to about 600 μm thick.

8. The sanitary ware of claim 1, wherein the top glaze layer is from about 25 μm to about 250 μm thick.

9. The sanitary ware of claim 1, wherein the top glaze layer is from about 25 μm to about 150 μm thick.

10. The sanitary ware of claim 1, wherein the top glaze layer is from about 100 μm to about 200 μm thick.

11. The sanitary ware of claim 1, wherein the top glaze layer is from about 150 μm to about 300 μm thick.

12. The sanitary ware of claim 1, wherein the top glaze layer is from about 200 μm to about 300 μm thick.

13. The sanitary ware of claim 1, wherein a top 10 μm of the top glaze layer contains more than 8 weight percent and less than 35.0 weight percent ZnO.

14. The sanitary ware of claim 1, wherein a top 10 μm of the top glaze layer contains more than 8 weight percent and less than 15.0 weight percent ZnO.

15. The sanitary ware of claim 1, wherein the top glaze layer includes a source of ions selected from one or more of Hg, Ag, Cu, Fe, Pb, Bi, and rare earths.

16. Sanitary ware comprising a multilayer antimicrobial ceramic glaze, the ceramic glaze comprising
   a base glaze layer containing from 0.0 percent by weight to about 8.0 percent by weight ZnO; and
   a top glaze layer containing from about 8.0 percent by weight to about 35.0 weight percent ZnO,
   wherein a top 10 μm of the top glaze layer contains more than 8 weight percent and less than 35.0 weight percent ZnO.

17. The sanitary ware of claim 16, wherein a top 10 μm of the top glaze layer contains more than 8 weight percent and less than 15.0 weight percent ZnO.

18. The sanitary ware of claim 16, wherein the top layer contains from about 10.0 weight percent to about 25.0 weight percent ZnO.

19. The sanitary ware of claim 16, wherein the base glaze layer is from about 300 μm to about 1000 μm thick.

20. The sanitary ware of claim 16, wherein the top glaze layer is from about 25 μm to about 300 μm thick.

21. The sanitary ware of claim 16, wherein a total ZnO content in the multilayer glaze is less than 5.0 weight percent.

\* \* \* \* \*